United States Patent [19]

Biermans et al.

[11] Patent Number: 4,572,676
[45] Date of Patent: Feb. 25, 1986

[54] METHOD AND APPARATUS FOR DETERMINING THE SATURATION TEMPERATURE OF A SOLUTION

[75] Inventors: Andreas J. Biermans, Urmond; Henk C. Burks, Oirsbeek; Karel G. H. Raemaekers, Munstergeleen, all of Netherlands

[73] Assignee: Unie van Kunstmestfabrieken B.V., Utrecht, Netherlands

[21] Appl. No.: 515,502

[22] Filed: Jul. 20, 1983

[30] Foreign Application Priority Data

Jul. 28, 1982 [NL] Netherlands ............... 8203013

[51] Int. Cl.[4] .................... G01J 5/58; G01N 25/12
[52] U.S. Cl. .................... 374/17; 250/225; 356/366; 374/20
[58] Field of Search ........... 374/16, 17, 19; 356/30, 356/366; 73/64.1; 250/225, 573

[56] References Cited

U.S. PATENT DOCUMENTS

| | | | |
|---|---|---|---|
| 2,716,371 | 8/1955 | Still | 374/17 |
| 3,008,324 | 11/1961 | Rayford et al. | 73/53 X |
| 3,026,710 | 3/1962 | Lupfer | 374/17 |
| 3,060,318 | 10/1962 | Ouvrard | 374/17 X |
| 3,187,557 | 6/1965 | Holbourne | 374/19 |
| 3,540,826 | 11/1970 | Bisberg | 374/19 X |
| 3,545,254 | 12/1970 | Chassagne et al. | 374/17 |
| 3,807,865 | 4/1974 | Gordon et al. | 374/17 |
| 3,875,788 | 4/1975 | Mills | 73/64.1 X |
| 3,947,120 | 3/1976 | Bar-Issac et al. | 356/30 |
| 4,377,001 | 3/1983 | Takeda et al. | 374/17 |
| 4,519,717 | 5/1985 | Jones et al. | 374/20 X |

Primary Examiner—Daniel M. Yasich
Attorney, Agent, or Firm—Cushman, Darby & Cushman

[57] ABSTRACT

A method and apparatus for determining the saturation temperature of a solution containing a dissolved substance, the crystals of which are optically anisotropic. The solution is placed in an optical measurement vessel under conditions wherein crystals of said substance are present, and the temperature of said crystal containing solution is gradually increased to at least the temperature at which all of the crystals dissolve. The temperature of the solution is continuously measured. Simultaneously with the temperature increase, a beam of linearly polarized light is directed into the optical measurement vessel in a manner such that it is transmitted through said solution; the transmitted beam of light, after having passed through the solution, is directed through a light polarizing analyzer having a direction of polarization normal to that of said beam of light; and at least a portion of any light transmitted through said analyzer is directed to a light measuring photodetector. Any light passing through crystals while present in the solution is optically rotated such that it is transmitted through the analyzer to the measuring photodetector, and the intensity of the transmitted light reaching said photodetector decreases to a lower, substantially constant level when all of the crystals have dissolved. The saturation temperature is the temperature of the solution at the time the light measured by the photodetector reaches this lower, substantially constant level.

8 Claims, 2 Drawing Figures

METHOD AND APPARATUS FOR DETERMINING THE SATURATION TEMPERATURE OF A SOLUTION

BACKGROUND OF THE INVENTION

The invention relates to a method for determining the saturation temperature of a solution in which the temperature of the solution in an optical measurement vessel is gradually increased from a temperature at which the solution contains crystals of the dissolved substance to a temperature at which all crystals are dissolved, the temperature meanwhile being measured continuously, a beam of light is transmitted through the measurement vessel and the dissolution of the last crystals present is detected optically.

Such a method is known from United Kingdom patent application No. 2,072,845. In said known method a beam of normal white light is used and the increase in intensity of the transmitted beam of light is detected at the moment the last (light-absorbing and scattering) crystals dissolve. The disappearance of the last crystals brings about only a slight increase of the light intensity, and therefore the moment at which this happens and the pertaining temperature cannot be determined fully accurately.

BRIEF DESCRIPTION OF THE INVENTION

The object of the invention is to provide a process in which the drawback of the prior art method referred to above has been eliminated.

The method according to the invention is characterized in that the beam of light is a linearly polarized beam of light and that the transmitted beam of light is made to pass through an analyzer the direction of polarization of which is normal to that of the beam of light, the intensity of the light transmitted through the analyzer is measured using a photodetector and said temperature is determined at the moment this intensity has reached a low, substantially constant value.

The method according to the invention can be applied in all those cases in which the crystals of the dissolved substance are optically anisotropic, that is, in general, when the crystals are not cubic. The method is based on the fact that in an anisotropic crystal, placed in a beam of linearly polarized light, the polarization plane of the light transmitted through the crystal is rotated (except in the exceptional case that the crystal has an optical axis exactly parallel to the beam of light). The direct beam is not allowed to pass through by the analyzer, but the light of which the polarization plane has been rotated in any crystals present is partially allowed through by the analyzer, so that the photodetector behind the analyzer measures a certain light intensity. When the last crystals have dissolved, virtually no more light will reach the detector. The method according to the invention has the advantage that measurements can be performed in turbid solutions, because non-anisotropic particles do not interfere with the measurement.

For generating the linearly polarized beam of light, use can be made of all means usually employed for the purpose, for instance a light source with an optical system and a polarization filter. According to the invention, however, by preference use is made of a laser, with which a narrow, well-defined, accurately parallel, intensive, virtually completely linearly polarized beam of light is obtained. As analyzer use is made of, for instance, a polarization filter or a Nicol prism.

As described, the saturation temperature is measured as that temperature at which, upon a gradual temperature increase, the last crystals dissolve, and not the temperature at which, upon a gradual decrease in temperature, the first crystals crystallize out, as the latter temperature, because of possible oversaturation of the solution, will in many cases not be the true saturation temperature.

The solution to be examined usually contains no crystals. In that case, the method according to the invention is carried out so that the solution not containing any crystals is fed to the measurement vessel, the light intensity measured by the photodetector having the said low, essentially constant value because the beam of light passes the clear solution without being hindered, but is not allowed to pass through by the analyzer. Subsequently the temperature of the measurement vessel is gradually decreased until crystals form, and this causes the light intensity measured by the photodetector first to increase, because in the crystals being formed the polarization plane of the transmitted light is rotated so that light passes the analyzer, and subsequently to decrease to a small value, because the light is strongly scattered in the denser crystal mass. After that, the temperature of the measurement vessel is gradually raised until the crystals dissolve and this causes the light intensity measured by the photodetector first to increase, namely when the light-scattering crystal mass has largely dissolved but crystals are still present in which the polarization plane of the light is rotated, and then to decrease to the low, constant value mentioned. As discussed above, the temperature at which this occurs is the saturation temperature to be determined.

To follow the formation and disappearance of the crystal mass, according to the invention a part of the beam of light transmitted through the measurement vessel can be split off, and its intensity measured with a second photodetector. When a light-scattering crystal mass is present in the measurement vessel, the intensity measured by the second photodetector is low; when no crystal mass is present, this intensity is high.

The use of a second photodetector also provides an attractive opportunity to control the temperature of the measurement vessel, this comprising decreasing the temperature of the measurement vessel as long as the light intensity measured by the second photodetector is at least equal to a certain high value and increasing it as long as the light intensity measured by the second photodetector is at most equal to a certain low value.

The method according to the invention can be carried out so that it is suitable for continuously measuring and monitoring the saturation temperature of a solution, for instance a process fluid in a chemical plant, this comprising continuously leading a small sample flow of solution to be examined through the measurement vessel and, also continuously, gradually decreasing the temperature of the measurement vessel until crystals form and, alternately, increasing it until the crystals have dissolved.

The method according to the invention proves to be very suitable for monitoring the saturation temperature of, for instance, an ammonium carbamate-containing aqueous solution formed in the preparation of urea or an ammonium nitrate-containing solution formed in the preparation of ammonium nitrate or ammonium nitrate-containing fertilizers or a digestion liquor obtained in the digestion of rock phosphate with nitric acid.

The invention also relates to an apparatus for carrying out the method according to the invention for determining the saturation temperature of a solution, provided with an optical measurement vessel, means for varying the temperature of the measurement vessel, means for measuring the temperature of the measurement vessel, means for generating a beam of light transmitted through the measurement vessel, and a photodetector for measuring the intensity of the transmitted light.

The apparatus according to the invention is characterized in that the means for generating the beam of light are capable of generating a linearly polarized beam of light and that an analyzer is placed in the transmitted beam of light before the said photodetector, the direction of polarization of said analyzer being normal to that of the beam of light. By preference, the means for generating a linearly polarized beam of light consist substantially of a laser. Further it is preferred to install a beam-splitting element in the transmitted light beam, between the measurement vessel and the analyzer, which element casts a part of the transmitted light onto a second photodetector.

The beam-splitting element may, for instance, be a semi-transparent mirror placed at an angle of 45° to the beam, or a divided rectangular prism, the plane of division of which has a semi-transparent mirror surface and is at an angle of 45° to the rectangular faces of the prism and to the beam.

The apparatus according to the invention may be provided with control means that receive a signal from the second photodetector and that control the means for varying the temperature of the measurement vessel in such a way that the temperature of the measurement vessel is decreased when the light intensity measured by the second photodetector is at least equal to a certain high value and is increased when the light intensity measured by the second photodetector is at most equal to a certain low value.

DETAILED DESCRIPTION OF THE INVENTION

The method and apparatus of the present invention will be discussed in greater detail in terms of the specific embodiments illustrated in FIG. 1. The method and the operation of the apparatus will be further elucidated with the aid of FIG. 2.

Figure 1:
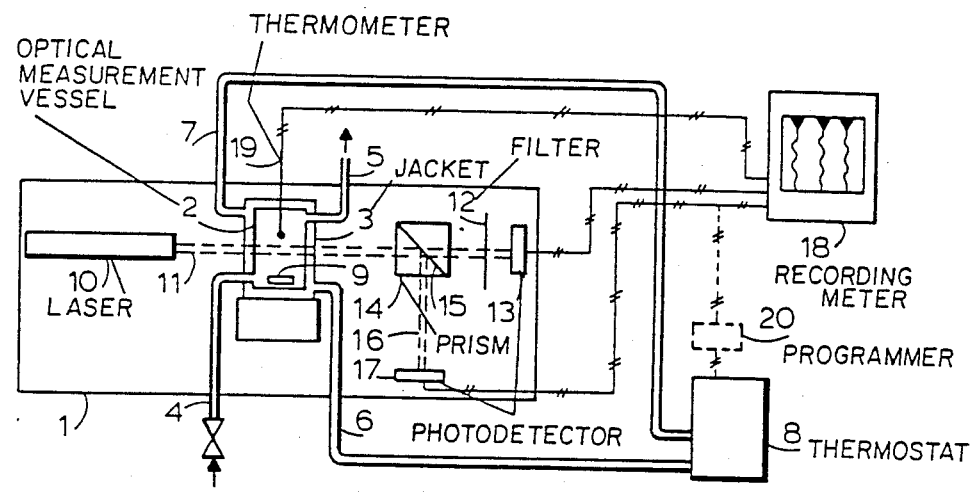
FIG. 1: a diagrammatic representation of an apparatus according to the invention by way of non-restrictive example.

In FIG. 1, 1 indicates a preferably light-tight cabinet in which the optical part of the device is placed. Via a supply line 4 a solution to be examined can be supplied to optical measurement vessel 2. Measurement vessel 2 is provided with a heating and cooling jacket 3 with a supply 6 and a discharge 7 for cooling and heating fluid. Using a programmed thermostat 8, the temperature of this fluid can alternately be decreased and increased, so that the solution in measurement vessel 2 is by turns cooled to below the saturation temperature and heated to above the saturation temperature. The solution in measurement vessel 2 is stirred continuously by means of a magnetic stirrer 9.

A laser 10 casts a beam of linearly polarized light 11 through measurement vessel 2. In the path traversed by the transmitted light a divided rectangular prism 14 has been placed, the plane of division 15 of which has a semi-transparent mirror surface and is at an angle of 45° to the transmitted beam. This prism casts part 16 of the transmitted radiation onto a photodetector 17; the remaining part of the transmitted beam falls on a polarization filter or analyzer 12 of which the direction of polarization is normal to that of the beam of polarized light 11 that is generated by laser 10. If light is present which can pass this polarization filter 12, it will fall on a photodetector 13.

The temperature of the solution in measurement vessel 2 is measured by an electrical temperature-measuring device 19, the sensitive part of which is placed as close as possible to the beam of light in vessel 2.

The output signals of photodetectors 13 and 17 and temperature-measuring device 19 are recorded by means of a multipoint recording meter 18.

Figure 2:
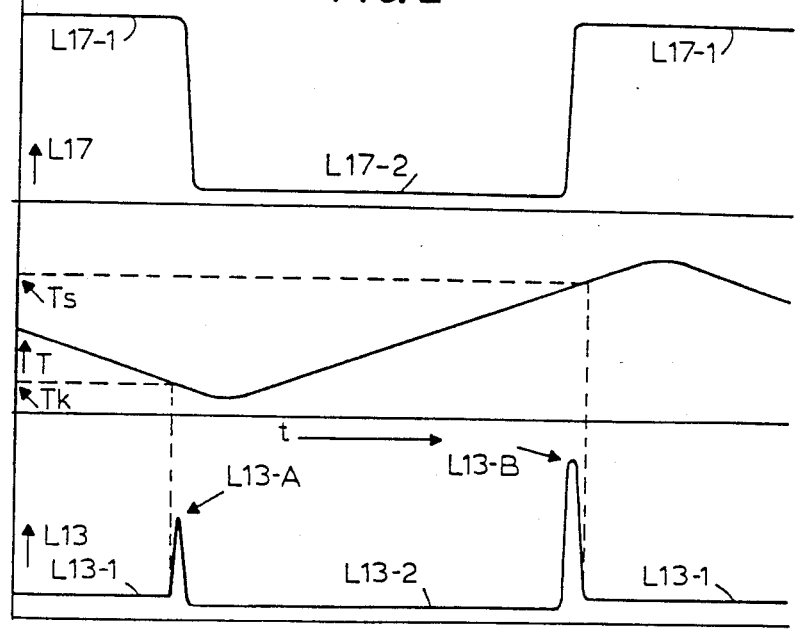
FIG. 2: the idealized pattern of the changes in the temperatures and light intensities measured during a measurement cycle.

In FIG. 2 the pattern of the changes in the variables measured during a measurement cycle is presented in idealized form. Horizontally, the time t is plotted, vertically the light intensity L13 measured by photodetector 13 (bottom graph), the temperature T measured by temperature-measuring device 19 (center graph) and the light intensity L17 measured by photodetector 17 (top graph).

A measurrement cycle comprises the following:

To measurement vessel 2 a clear solution is supplied. Polarization filter 12 does not allow the light of the laser to pass, so that the light intensity L13 that is measured by photodetector 13 has the low, virtually constant value L13-1; the light intensity measured by photodetector 17 has the high value L17-1.

The temperature of the solution is now gradually decreased, and at a temperature $T_k$ the dissolved substance starts to crystallize out. In the case presented here the solution has become supercooled, so that $T_k$ is not the true saturation temperature. Because, as long as the amount of crystals is small, light of which the polarization plane has been rotated in the crystals passes through polarization filter 12, L13 increases rapidly to a peak value L13-A, and then decreases to the small value L13-2 as the light is largely scattered in the denser crystal mass; L17 decreases to the low value L17-2.

Subsequently, the temperature of the solution is gradually increased until the crystals redissolve. When the crystal mass has for the larger part dissolved, but crystals are still present, L13 increases to a peak value L13-B and subsequently decreases, when the last crystals dissolve, to the low, constant value L13-1. The temperature $T_s$, at which the last crystals dissolve, is the saturation temperature to be determined. Upon dissolution of the crystals L17 has again assumed its high value L17-1.

The determination can be carried out both discontinuously and continuously. For discontinuous determination vessel 2 is filled with sample solution and then closed, after which the determination is performed in the way described. Subsequently the sample is discharged, vessel 2 is, if necessary, flushed and a new sample is or is not supplied. For continuous determination a small sample flow is continuously supplied and the temperature of the solution is alternately decreased until crystals form and increased until the crystals dissolve; the amount of sample supplied per unit of time then is to be taken so small that the desired temperature program is not interfered with.

For the actual determination of the saturation temperature only signals T and L13 are used. Signal L17, however, gives a good indication of the reliability of the measurement; a deviating signal L17 may for instance point to defects or fouling of the equipment, or to the presence of non-soluble, suspended solid components. Signal L17 can be used to control the temperature program of thermostat 8. In FIG. 1 this alternative is indicated by the broken lines; a programmer 20 controls thermostat 8 in such a way that the temperature of the measurement vessel 2 is decreased as long as signal L17 has the high value L17-1 and increased when the signal L17 has the low value L17-2.

We claim:

1. Apparatus for determining the saturation temperature of a solution by optically detecting the dissolution of crystals in said solution as the solution temperature is varied, comprising
   an optical measurement vessel adapted to contain said solution,
   means for varying the temperature in said vessel,
   means for measuring the temperature in said vessel,
   means for generating a linearly polarized beam of light,
   means for transmitting said beam of light through solution contained in said measurement vessel,
   first and second photodetector means for measuring light intensity of at least a portion of said beam of light,
   beam-splitting means positioned in said transmitted beam of light adapted to split said transmitted beam of light into at least two portions and to direct a first portion thereof onto said first photodetector means, and a second portion thereof onto said second photodetector means,
   control means adapted to receive a signal from said second photodetector means and to responsively control said temperature varying means such that the temperature in said measurement vessel is caused to decrease when the light intensity measured by said second photodetector means remains at or above a preselected high value and is caused to increase when the light intensity measured by said second photodetector means remains at or below a preselected low value,
   a light polarizing analyzer positioned in said first portion of said transmitted light between said beam-splitting means and said first photodetector means, the direction of polarization of said analyzer being normal to that of said transmitted beam of light, whereby signals from said first photodetector means and said temperature measuring means are used to determine the saturation temperature of said solution.

2. Device according to claim 1, wherein the means for generating a linearly polarized beam of light consist substantially of a laser.

3. A method for determining the saturation temperature of a solution containing a dissolved substance, the crystals of which are optically anisotropic, comprising the steps of placing said solution in an optical measurement vessel under conditions wherein no crystals are present, gradually decreasing the temperature of said solution until said crystals are formed and thereafter gradually increasing the temperature of said crystal containing solution until said crystals dissolve while continuously measuring said temperature, and simultaneously with said temperature decrease and increase
   directing a beam of linearly polarized light into said optical measurement vessel in a manner such that it is transmitted through said solution,
   directing said transmitted beam of light, after having passed through said solution, through beam-splitting means whereby said transmitted beam is split into at least two portions,
   directing a first portion of said split transmitted beam through a light polarizing analyzer having a direction of polarization normal to that of said beam of light, and directing at least a portion of any light transmitted through said analyzer to said first photodetector by means of which its intensity is measured,
   directing a second portion of said split transmitted beam to a second photodetector by means of which its intensity is measured,
   gradually decreasing the temperature of said solution so long as the light intensity measured by said second photodetector remains at or above a preselected high value,
   gradually increasing the temperature of said solution so long as the light intensity measured by said second photodetector remains at or below a preselected low value,
whereby light passing through any said crystals while present in said solution is optically rotated such that it is transmitted through said analyzer to said first photodetector, and, while the temperature of said solution is gradually increased, the intensity of said transmitted light measured by said first photodetector decreases to a lower, substantially constant level when all of said crystals have dissolved, said saturation temperature being the temperature of said solution at the time the intensity of light measured by said first photodetector reaches said lower, substantially constant level.

4. The method of claim 3 wherein the source of said linearly polarized beam of light is a laser.

5. The method of claim 3 wherein a sample flow of said solution is continuously passed through said measurement vessel and the temperature of said solution in said measurement vessel is alternately gradually decreased until said crystals form and increased until said crystals have dissolved.

6. The method of claim 3 wherein said solution is an aqueous solution containing ammonium carbamate.

7. The method of claim 3 wherein said solution is an aqueous solution containing ammonium nitrate.

8. The method of claim 3 wherein said solution is a digestion liquor obtained in the digestion of rock phosphate with nitric acid.

* * * * *